US009011145B2

(12) United States Patent
Hang

(10) Patent No.: US 9,011,145 B2
(45) Date of Patent: Apr. 21, 2015

(54) MAXILLARY EXPANSION AND ADVANCEMENT ORTHODONTIC APPLICANCE

(76) Inventor: William M. Hang, Westlake Village, CA (US)

( * ) Notice: Subject to any disclaimer, the term of this patent is extended or adjusted under 35 U.S.C. 154(b) by 741 days.

(21) Appl. No.: 12/731,649

(22) Filed: Mar. 25, 2010

(65) Prior Publication Data
US 2011/0236847 A1 Sep. 29, 2011

(51) Int. Cl.
*A61C 3/00* (2006.01)
*A61C 7/10* (2006.01)

(52) U.S. Cl.
CPC .......................................... *A61C 7/10* (2013.01)

(58) Field of Classification Search
CPC .............. A61C 7/08; A61C 7/00; A61C 7/10
USPC ........................................................ 433/6, 7
See application file for complete search history.

(56) References Cited

U.S. PATENT DOCUMENTS

| 3,434,210 | A | | 3/1969 | Sage | |
|---|---|---|---|---|---|
| 3,454,001 | A | | 7/1969 | Stockfisch | |
| 4,026,023 | A | * | 5/1977 | Fisher | 433/7 |
| 4,054,996 | A | | 10/1977 | Wallshein | |
| 4,468,196 | A | | 8/1984 | Keller | |
| 4,573,914 | A | | 3/1986 | Nord | |
| 5,002,485 | A | * | 3/1991 | Aagesen | 433/7 |
| 5,087,196 | A | | 2/1992 | Polanco | |
| 5,096,416 | A | * | 3/1992 | Hulsink | 433/6 |
| 5,131,843 | A | | 7/1992 | Hilgers et al. | |
| 5,368,477 | A | | 11/1994 | Neeley | |
| 5,829,970 | A | | 11/1998 | Yousefian | |
| 6,213,766 | B1 | | 4/2001 | Di Massa | |
| 6,435,871 | B1 | * | 8/2002 | Inman | 433/7 |
| 2008/0057457 | A1 | * | 3/2008 | Inman | 433/6 |
| 2008/0220388 | A1 | * | 9/2008 | Weissbach Otte | 433/7 |

* cited by examiner

*Primary Examiner* — Cris L Rodriguez
*Assistant Examiner* — Matthew Nelson
(74) *Attorney, Agent, or Firm* — Sanford Astor; Brooks Kushman P.C.

(57) ABSTRACT

A palatal expansion orthodontic appliance comprising, an advancer for advancing the upper front teeth, an expansion screw for controlling the expansion of two acrylic halves that each contain a Hang Clasp and optionally a molar intrusion wire. The two acrylic halves share and anchor the wire ends of the advancer, the Hang clasps and any molar intrusion wires. The orthodontic appliance simultaneously expands the maxillary arch and advances the upper front teeth. Methods of manufacture, including kits for the manufacture of the orthodontic appliance are also included.

6 Claims, 8 Drawing Sheets

MAXILLARY EXPANSION AND ADVANCEMENT ORTHODONTIC APPLICANCE

FIELD OF THE INVENTION

This invention relates to a new and useful type of orthodontic appliance that functions as both an expander of the maxillary arch and an advancer of the upper front teeth.

BACKGROUND OF THE INVENTION

Heretofore, orthodontic devices have included such devices as expanders, for expanding the maxillary arch, and other devices such as traditional braces for advancing the front teeth. Optimal treatment of a patient may often require both expansion and advancement. Present practice is expensive, inconvenient, inefficient, and requires excessive time for effective treatment.

Various devices for expanding the maxillary arch by causing lateral movement of the molars and bicuspids, and possibly the canines, have been disclosed, These include those shown in the Fisher U.S. Pat. No. 4,026,023 and the Nord U.S. Pat. No. 4,573,914. Fisher's device uses a series of closed flap springs to push against and move certain individual teeth, including the incisors. The Nord device utilizes bands which are cemented to the molars. The device also has an arch wire that presses against the lingual surfaces of the incisors.

John Mew's Stage I Biobloc appliance can simultaneously advance the front teeth while expanding the maxilla laterally. The Stage I Biobloc uses a Crozat Clasp, whereas the present Orthodontic Appliance uses a Hang Clasp in its place, and the Stage I Biobloc has a very different appearance from that of the orthodontic appliance of this invention. Mew's Stage 1 Biobloc has five (5) wires to advance and align the incisor teeth, whereas the present orthodontic appliance has one advancing wire. It is much simpler to adjust the one wire than to simultaneously adjust five wires.

A three-way sagittal appliance can also simultaneously advance the front teeth while expanding the maxilla laterally. The advancement is done with two (2) screws which, with the usually accepted activation schedule (one activation every four days), will take more than twice as long to advance the teeth as the present invention.

Each of these above-mentioned devices are all deficient in being able to expand the maxilla laterally and advance the maxillary anterior teeth to their proper position in space at the same time.

SUMMARY OF THE INVENTION

The present invention is a new and useful orthodontic appliance that effectively and efficiently combines an orthodontic expander device and an orthodontic advancer device into a single, effective orthodontic appliance. This orthodontic appliance is effective in treating patients in need of expanding the maxillary arch and advancing the upper front teeth, using a convenient, single orthodontic appliance. While this orthodontic appliance may be utilized for a patient with all permanent teeth, this appliance is especially useful for children who still have primary teeth as well as permanent teeth. The appliance of this invention is useful and effective to accomplish craniofacial modification. Correction of patients with a maxillary deficiency or malocclusion can receive significant benefits from early treatment with the appliance of this invention.

A preferred embodiment of this orthodontic appliance uses a new and useful clasp, referred to as the "Hang Clasp", also invented by the present inventor. An advantage of using the Hang Clasp is that, even if its weld/solder joint fails or breaks, the Hang Clasp maintains its form and functionality for several days or longer, until the break is repaired by an orthodontist. Both the orthodontic appliance and the Hang Clasp are significant advances in the art, as described further herein.

The use of the Hang Clasp gives the appliance of this invention superior retentive strength to orthodontic appliances now in use. Many present appliances use a Crozat Clasp, which provides no retention at all if its solder joint breaks, since the clasping part then falls off entirely. An orthodontic appliance using the Crozat Clasp will then fall out of the mouth. The Hang Clasp will continue to provide retention if the weld/solder joint breaks, for example, due to metal fatigue, since the retaining parts of the Hang Clasp, the two Hang Clasp anchors, are still present and embedded in an acrylic half of the orthodontic appliance, as described below. If the Hang Clasp breaks, no time is lost in treatment, since the appliance can still be worn until any needed repair is made during an office visit to the Orthodontist. Alternate clasps do not have this advantage, and there may be considerable time lost in treatment. During the course of orthodontic treatment, adjustments to the orthodontic appliance are routinely made for treatment to progress. The Crozat Clasp has a significant chance of breakage when such adjustments are made using pliers, the instrument of choice for making such adjustments. The Hang Clasp has a significantly reduced chance of breakage when adjusted with pliers.

Another clasp, known as the Adams Clasp, is commonly used in removable orthodontic appliances, but has poor retention, and is difficult to adjust for better retention. The Hang Clasp is easy to adjust for optimal retention.

BRIEF DESCRIPTION OF THE DRAWINGS

The foregoing and other objects, features and advantages of the invention will be apparent from the following more particular description of the embodiments of the invention, as illustrated in the accompanying drawing figures.

Figure 1:
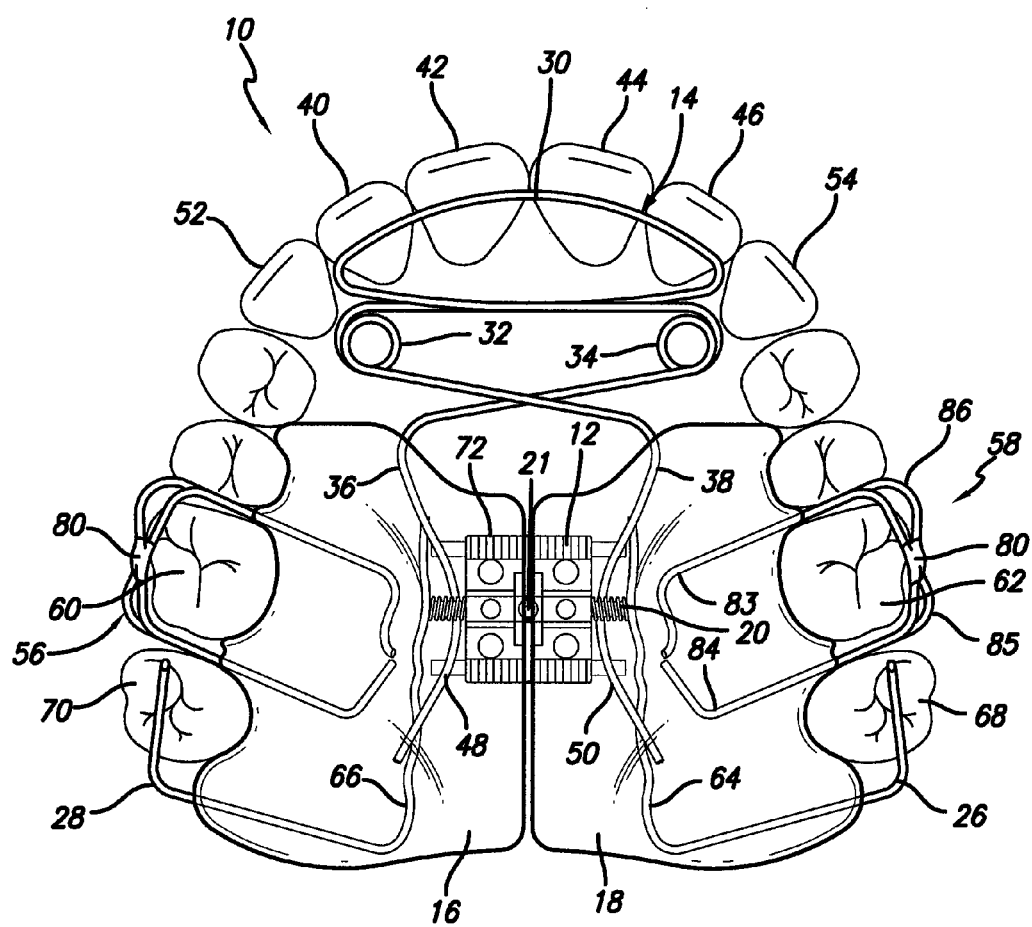
FIG. 1 is a bottom plan view of a preferred embodiment of the invention.

The numerals in the drawings refer to the same parts or elements of the invention, throughout the different views and the specification. The drawing figures are not necessarily drawn to scale, as emphasis is instead being placed upon illustrating the principles of the invention. The views are essentially illustrating a preferred embodiment of the invention, and its essential parts or elements, and are shown in a non-adjusted position. When the appliance is prepared for a patient, elements of the appliance are adjusted by the orthodontist to precisely fit the patient. Therefore, there may be some variance in the relative size and position of the elements of the invention.

DETAILED DESCRIPTION OF THE INVENTION

Referring now to the drawings, there is shown the orthodontic appliance (10) of the invention comprising an expansion assembly (12) and an advancer (14) embedded into each of two acrylic palatal halves (16, 18) of the appliance, thereby holding the two halves firmly together as a single appliance contoured to the patient's hard palate. Expansion assembly (12) comprises a screw (20) which is turned to adjust the lateral movement of the two palatal halves (16, 18).

Appliance (10) further comprises two orthodontic clasps (56, 58) and two molar intrusion 100 wires (26, 28) one of each embedded into each side of the two acrylic palatal halves (16, 18).

The advancer (14) comprises a single wire wound into an advancing wire section (30), two advancing wire helix sections (32, 34), and two advancing wire anchor sections (36, 38).

The two advancing wire anchor sections (36, 38) are each embedded in and anchored to the separate acrylic halves (16, 18) and protrude from the front of each acrylic half (16, 18) then forming the two helix sections (32, 34) and the advancing wire section (30) which protrudes from the front of the appliance, in a generally half-oval shape, adapted to press against the back of the four incisors (40, 42, 44, and 46).

The two wire helices (32, 34) are located between the rear of the advancer wire (30) and the front of the wire anchors (36, 38). The helices (32, 34) provide a gentle force to the advancing wire section (30) on the upper front teeth (40, 42, 44, and 46). The upper front teeth, the incisors, (40, 42, 44, and 46) sometimes along with the two cuspids (52, 54) may be bonded together with braces (not shown), so that they are all pushed forward together by advancer (30).

Each of the two advancing wire anchors (36, 38) may have crimps (48, 50) or the like, near their terminal ends, to stabilize their set in their respective acrylic half (16, 18) effectively preventing the advancer (30) from coming loose or sliding out of one or both of the acrylic halves (16, 18).

Each of the two outer sides of the acrylic halves (16, 18) along their mid-regions, has an orthodontic clasp (56, 58) embedded therein. Clasps (56, 58) fit around a molar tooth, generally the primary second molar (60, 62) to help hold the entire appliance (10) in place.

Near the rear region of the side of each of the two acrylic halves (16, 18), there is a molar intrusion wire (26, 28). Each of the two molar intrusion wires (26, 28) has an anchor portion (64, 66) which is embedded and anchored to the rear portion of a separate acrylic half (16, 18). The anchor portion (64, 66) of the molar intrusion wire (26, 28) that is embedded in the acrylic half (16, 18) may be crimped to stabilize and secure its position. The molar intrusion wire (26, 28) sits on the top of a molar tooth (68, 70) and presses on the molar (68, 70) to intrude them into the gums of the patient, if such treatment is needed. If such treatment is not needed, intrusion wires (26, 28) are not present as a part of the orthodontic appliance.

The wire comprising the advancer (30) the orthodontic clasps (56, 58) and the molar intrusion wires (26, 28), and their associated elements and anchors, may be a heat-treated stainless steel wire with a gauge thickness of approximately 0.032 inch. The wire composition, and particularly its gauge thickness, may vary according to the needs of the patient and judgment of the Orthodontist. The wire gauge thickness may range from about 0.030 to about 0.036 inches, preferably about 0.032 inches.

An alternative to stainless steel wire is TMA wire (Titanium Molybdenum Alloy wire) with wire gauge thickness of about 0.030 to about 0.038 inches, preferably about 0.036 inches in diameter. TMA wire, which is available from Great Lakes Orthodontics, of Tonawanda, N.Y., is comprised essentially of Ti: 70-80%, Zr: 5-10%, Sn: 4-8%, and Mo: 10-20%. TMA wire provides a very light force for a given activation of advancement. It is much lighter than stainless steel for an equal amount of activation. TMA wire can make a larger activation which will result in a larger movement of the teeth with less discomfort to the patient. A less frequent appointment interval in which the patient needs to return to the office for additional activation is also an advantage. With one activation the teeth will move farther than with stainless steel.

Applicant has discovered that the TMA wire provides a lighter force on the teeth, which actually will move the teeth faster with less discomfort. The teeth move faster because less pressure is placed on the root/bone interface. Less pressure means less disruption to the blood supply of the tooth. More blood supply to the tooth means that the process of bone resorption, which makes the space into which the tooth will move, will occur faster. Greater forces essentially disturb the blood supply more and a new blood supply must be made through the bone to have the resorption process (osteoclastic activity) occur. Because the body must make a new blood supply to the area, there is a lag in tooth movement with heavier forces. There is a very big advantage to the patient including less discomfort and faster tooth movement with lighter forces.

The orthodontic appliance of this invention is typically composed essentially of acrylic, as noted above, and is formulated by combining a polymeric powder with a monomer liquid on an upper plaster model, taken of the patient to be fitted with the orthodontic appliance.

The mechanism portion (72) of the expansion assembly (12) that contains the adjustment mechanism (21) for screw (20) and the exposed elements of the orthodontic appliance, that are adjacent to the acrylic halves (16, 18) are coated and held in place with sticky wax, that may be removed with hot water or steam near the final stage of the manufacturing process. The polymer and monomer are then applied to the plaster model with the anchor elements of the appliance set in place, to be embedded securely in the acrylic palate of the orthodontic appliance. Once the acrylic is set and hardened, the acrylic palate is then manually cut, as desired, along its symmetric midline to form the aforementioned two acrylic halves (16, 18).

Various known clasps, such as the Adams clasp or the Crozat clasp, mentioned earlier, can be used to hold the appliance on the upper teeth. However, an improved, preferred clasp is the Hang Clasp (56, 58) which is embedded into the side of each of the two acrylic halves (16, 18).

Figure 9:
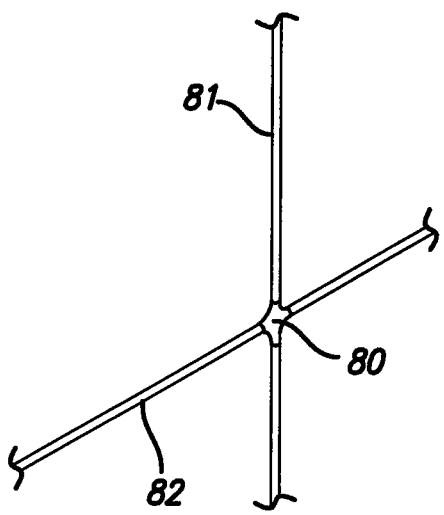
FIG. 9 is a top view of the Hang Clasp wires before they are bent into shape; and, FIG. 10 is a bottom plan view of the orthodontic appliance in the mouth of a youthful patient.

Referring now to FIGS. 6-9, there is shown one "Hang Clasp" (58) (shown in FIGS. 1-5 as clasps (56, 58) as used throughout this specification and refers to a new and useful element used with the present orthodontic appliance, and may be used with other orthodontic appliances. The Hang Clasp (58) as shown in FIGS. 6-9, is a welded and soldered two piece metal clasp. The clasp comprises two substantially equal length wires (81, 82) best seen in FIG. 9, soldered together at a point (80) to form two substantially equal length long ends (83, 84) and two substantially equal length short ends (85, 86) best seen in FIGS. 6, 7 and 8. The wires, as seen in FIG. 9, are bent into a shape adapted to create a clasp around a molar at their short end, as shown in FIGS. 1-5.

Wires (81, 82) are soldered together at point (80) about ¾ down the length of the wires, at adjacent angles that are typically about 45° and 135°, with a weld and silver solder joint (80) thereby causing four wire segments and their four wire ends to extend from the weld/solder joint (80). The four wire segments extending from the weld/solder joint (80) are the two tooth clasps (85, 86) and the two clasp anchors, the mesial wire (83) and the distal wire (84). Once the two wires are attached with a weld/solder joint (80) the four wire segments (83, 84, 85, 86) extending from the weld/solder joint (80) are each bent to form a clasp wire bend, so that the Hang Clasp (58) will fit around the patient's molar (60, 62).

The Hang Clasp (58) is held in place in the acrylic (16, 18) portion of the orthodontic appliance by embedding the two clasp anchors (83, 84) into the acrylic (16, 18). The two wires (85, 86) extending from the weld/solder joint (80) that are not embedded into the acrylic (16, 18) are the mesial clasp (86) and the distal clasp (85) which engage tooth (62) as shown in FIGS. 1-4.

The aforementioned angles, where the two wires are attached with a weld/solder joint (80) may vary significantly, according to the patient's needs, and may be, for example, approximately 20° and 160° to approximately 60° and 120°, as needed. The Hang Clasp (58) is so named because it is traditional for embodiments of medical devices, such as a new and useful type of orthodontic clasp, to be named after its inventor, in this case Dr. William M. Hang, the inventor of the present Hang Clasp (58) to distinguish it from other orthodontic clasps.

Heat treated stainless steel wire, of about 0.032 gauge, as previously described, is preferred for the Hang Clasp. The Hang Clasp is an incredibly strong clasp which makes the appliance very hard to remove from the mouth, a needed benefit. If the Hang Clasp should break, it will still function until it is repaired by the Orthodontist.

The orthodontic appliance has optionally, two molar intrusion wires (26, 28) designed to lie on each of the six-year molars, as shown in FIG. 1. The molar intrusion wire (26, 28) may be made of a 0.032 inch, heat treated, stainless steel wire, or 0.036 TMA wire, where one end of the molar intrusion wire (26, 28) lies on the occlusal surface of the six-year molar tooth (68) and the other end, being the molar intrusion wire anchor (64, 66) is embedded in the acrylic (16, 18). The molar intrusion wire (26, 28) and its associated molar intrusion wire anchor (64, 66) is shaped using a 3-prong pliers or the like. The portion of the molar intrusion wire anchor (64, 66) to be embedded in the acrylic (16, 18) is bent a plurality of times, using a 3-prong pliers or the like, to form a plurality of crimps, or the like. These crimps further prevent the molar intrusion wire (26, 28) from rotating or moving when embedded in the acrylic (16, 18).

Figure 2:
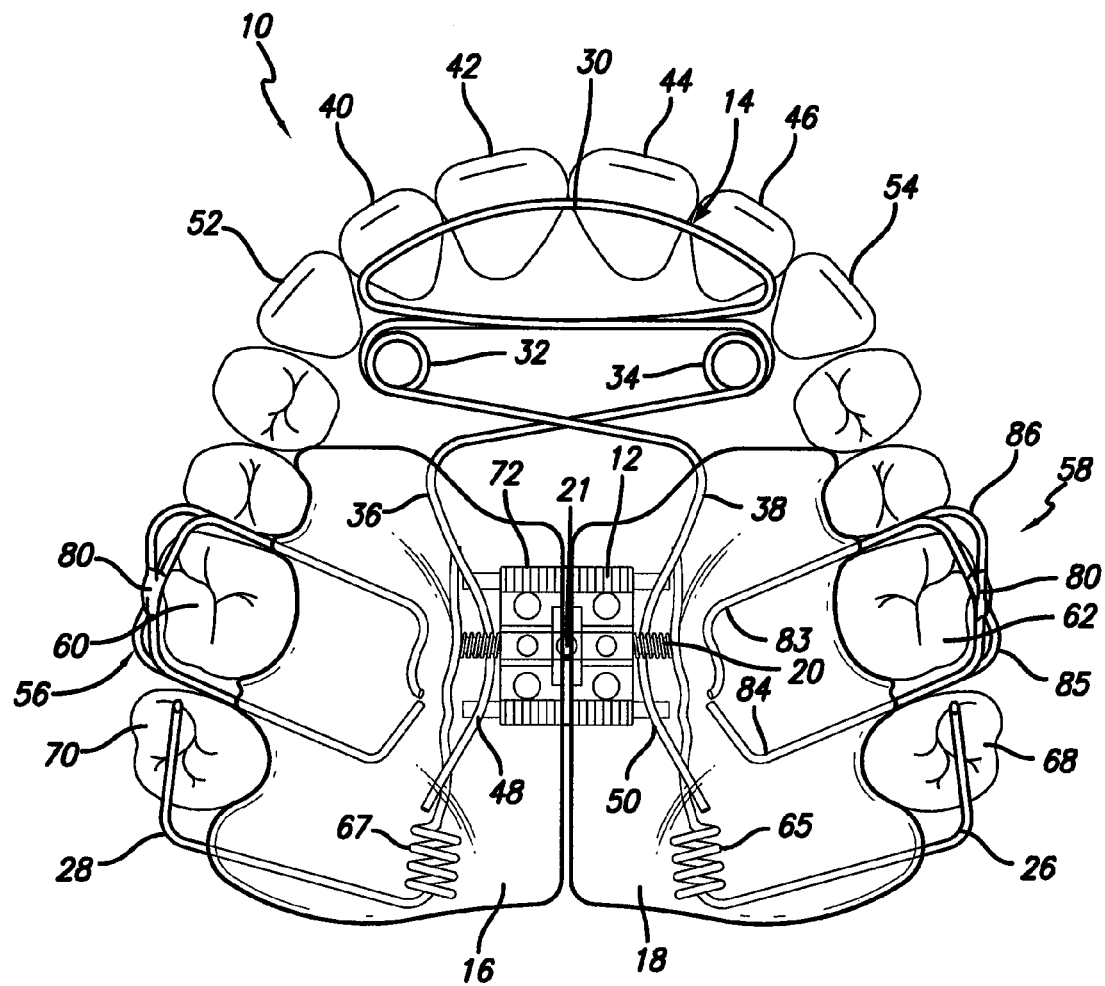
FIG. 2 is a bottom plan view of another embodiment of the invention.
Figure 3:
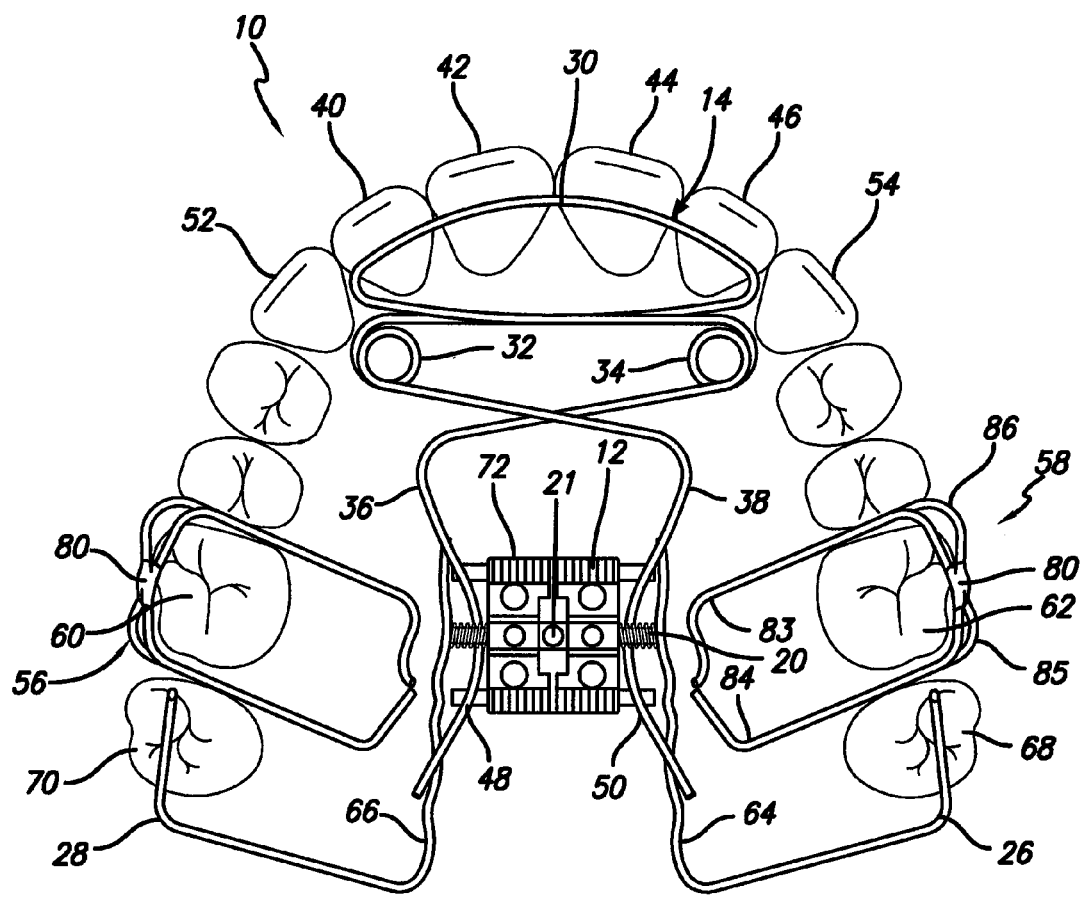
FIG. 3 is a bottom plan view of the embodiment of FIG. 1, with the acrylic body removed.
Figure 4:
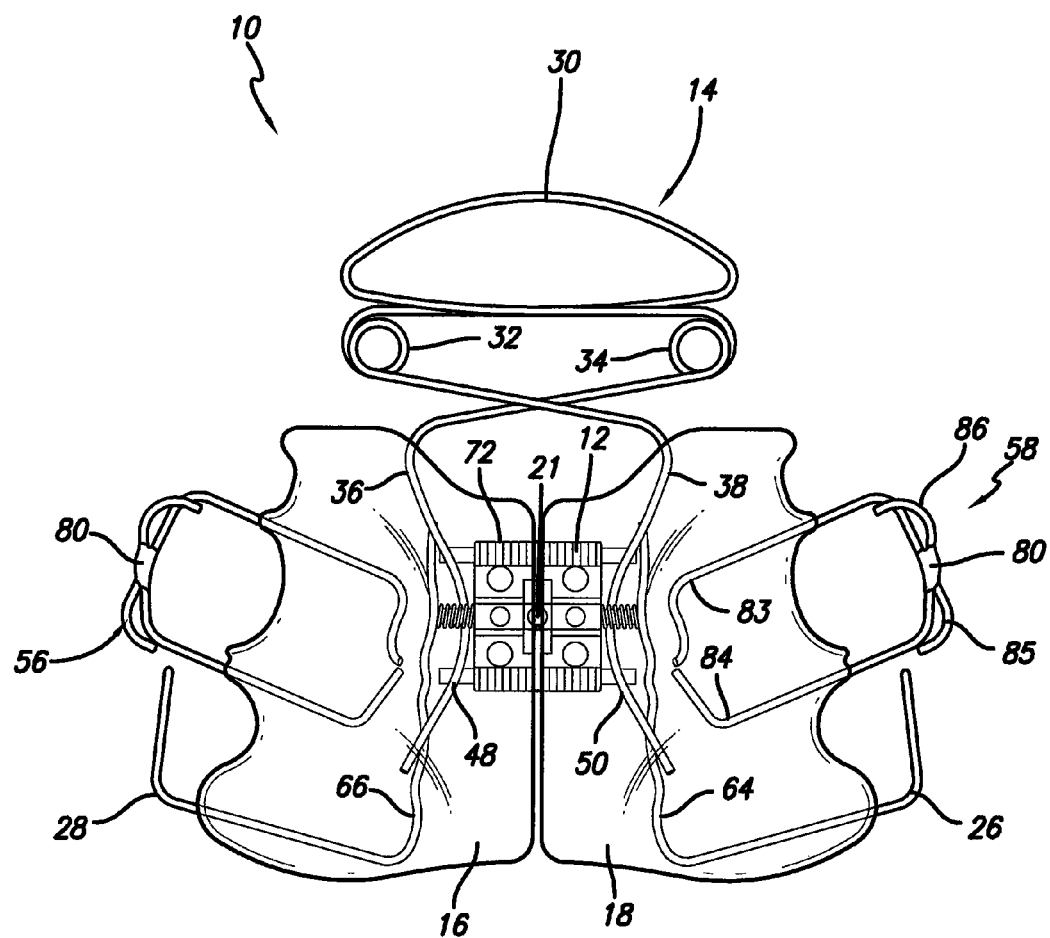
FIG. 4 is a bottom plan view of the embodiment of FIG. 1, with the depiction of the teeth removed.
Figure 5:
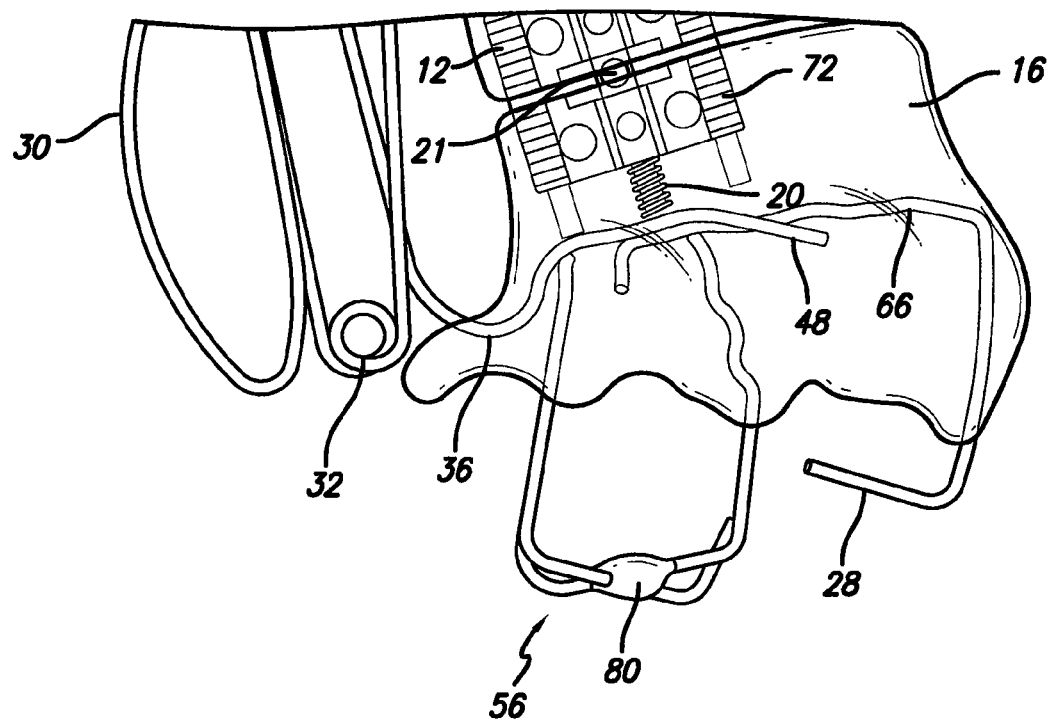
FIG. 5 is a perspective left side view of the embodiment of FIG. 1, the opposite view generally being a mirror image thereof.
Figure 6:
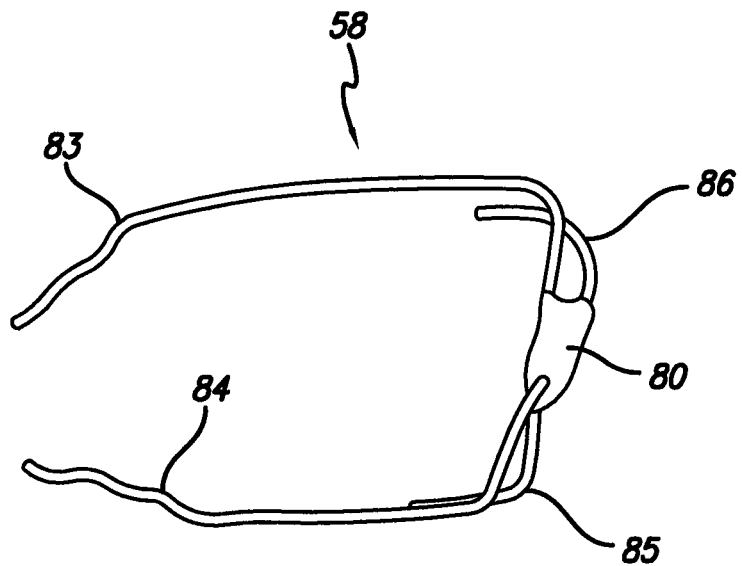
FIG. 6 is a top plan view of the Hang Clasp.
Figure 7:
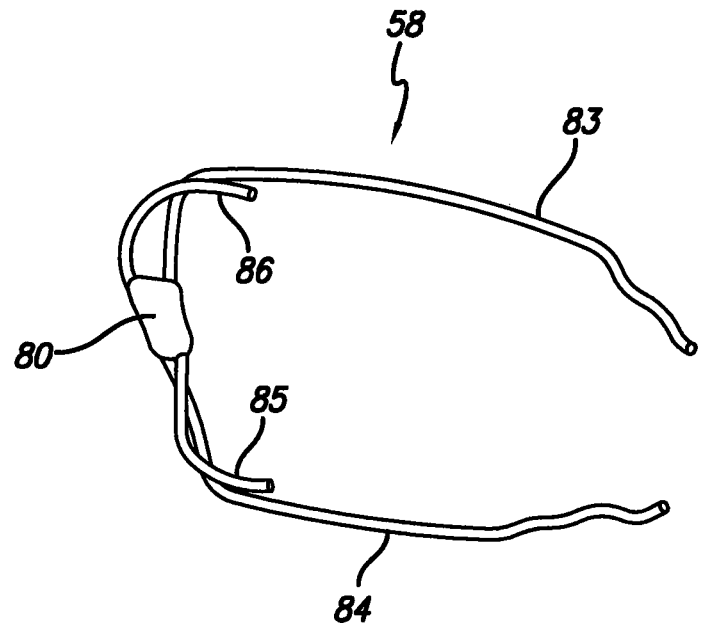
FIG. 7 is a bottom view of the Hang Clasp.
Figure 8:
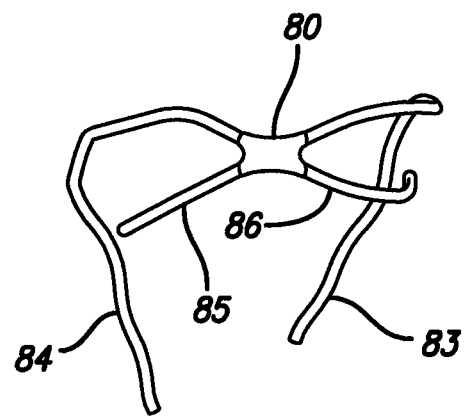
FIG. 8 is a perspective view of the Hang Clasp.

For some patients, it is necessary to intrude the first molars (move them straight back up into the bone). This requires a very gentle continuous force. The anchor wire may be relatively straight, as shown in FIG. 1, (64, 66) or it may have a helix bent into it, as shown in FIG. 2, (65, 67). The helix adds more wire, which dramatically drops the force on the tooth, particularly when using TMA wire, and increases the range of action of the wire with one activation. This means that the patient can often go 6-8 weeks without having to visit the orthodontist for additional activation.

Figure 10:
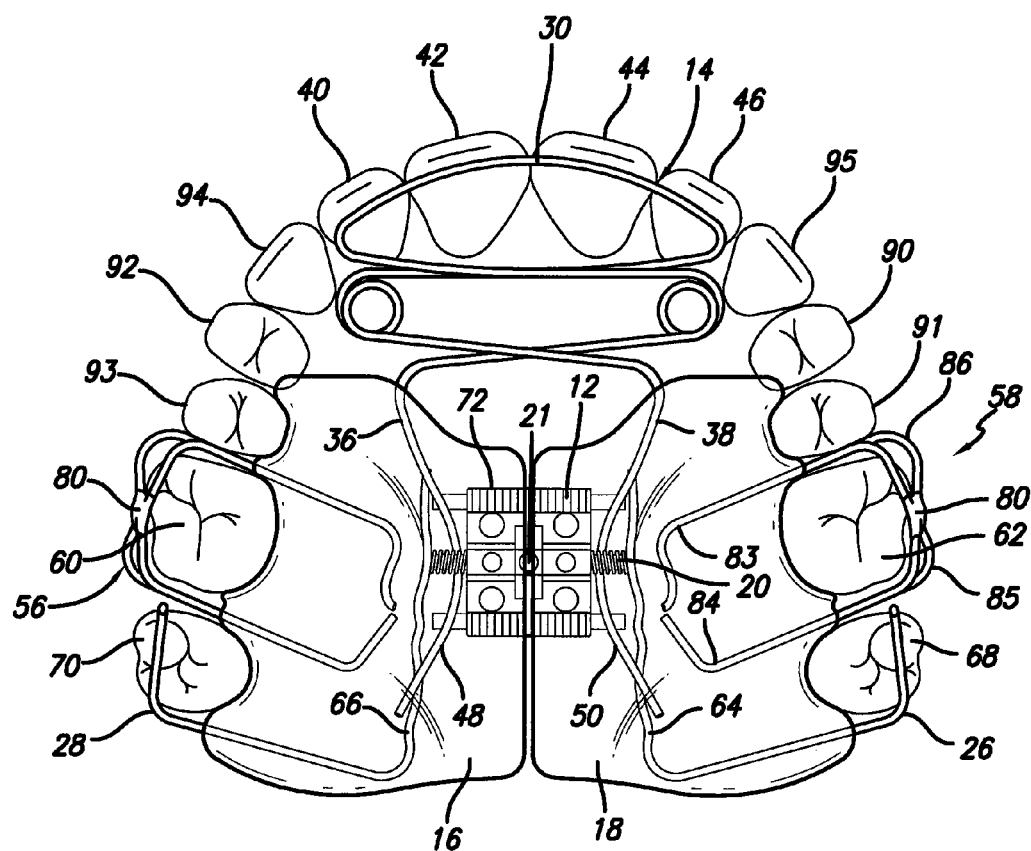

In FIGS. 1-4, the teeth are depicted to appear as permanent teeth which are perfect in location and state. This has been done to more easily show the orthodontic appliance of this invention. However, teeth are usually not in this condition, particularly when they need orthodontic treatment. Also, the treatments described herein are especially applicable to young persons, who are still growing and have a combination of primary and permanent teeth. FIG. 10 depicts the upper teeth of a patient who has both primary teeth (90, 91, 92, 93, 94, 95) and the rest, permanent teeth.

The term "acrylic" as used throughout this specification and its appended claims is intended to be broadly construed to include, essentially, a wide range of related polymeric 225 materials, some of which may not be chemically classified as an acrylic, but as a functionally equivalent chemical. The term "acrylic" is also intended to include chemical mixtures composed essentially of acrylic, but also optionally including other desirable chemicals and the like, such as colorants or dyes for adding a desired tint or color to the acrylic halves (16, 18) such as a blue or a light red color. The term "acrylic" is used herein, as that is the material of choice for the acrylic halves (16, 18) used in the orthodontic appliance, but includes other functionally equivalent polymeric materials. The acrylic formulation used in the manufacture of the orthodontic appliances disclosed throughout this specification and its appended claims typically use a cold-cured or salt-and-pepper method of forming the acrylic element of the orthodontic appliance. The acrylic element (16, 18) of the present orthodontic appliance is bisected along its midline, and said two acrylic halves (16, 18) are essentially held together as a single acrylic mold of an upper palate, with both the expansion screw (20) that is partially embedded into each of the two acrylic halves (16, 18) and the two advancing wire anchors (36, 38) that are each partially embedded into a separate acrylic half (16, 18).

The term "anchor" as used throughout this specification and its appended claims is intended to be broadly construed and is intended to logically classify the portion of the metal wires associated with some of the elements of the orthodontic appliance that are largely embedded in the acrylic halves (16, 18) with their terminal ends for support and to act as an anchor for the associated element of the invention. The various anchor wires embedded in the acrylic halves (16, 18) also serve to reinforce the structural strength of the acrylic halves (16, 18) and to prevent the acrylic halves from breaking, much as rebar is used to reinforce concrete.

The term "crimp" or "crimped" as used throughout this specification and its appended claims is intended to be broadly construed, and is intended to refer to portions of the wire elements of the invention that are generally embedded in an acrylic half and have one or more bends, wiggles, waves, or the like, with a plurality of such bends, wiggles, or waves being preferred. The crimps in an anchor wire may be along one plane or in some applications, may be generally along a plane and with some crimping also along a perpendicular plane. The crimps in the anchor portion of the wire elements of the invention are intended to help anchor and stabilize the element in the relevant acrylic half, and prevent the associated element from coming loose or changing its fixed position in the acrylic half. The crimps in an anchor element may or may not be slightly flattened, as desired by the orthodontist.

The terms "weld/solder", "weld/solder joint", "clasp weld/solder joint" are intended to be generally synonymous, and as used throughout this specification and its appended claims are intended to be broadly construed and are also intended to refer to the one or more weld joints in the Hang Clasp (56, 58) that are reinforced with a silver solder, or the like. The weld is made to tack the two wires (81, 82) in place to allow accurate placement of the wires for the solder joint. Although silver solder is preferred for the clasp weld/solder joint, in some embodiments of the orthodontic appliance, other safe and effective solder formulations may be used in the clasp weld/solder joint.

The term "expansion screw" as used throughout this specification and its appended claims is intended to be broadly construed, and includes a broad range of threaded or notch-based expansion devices used for orthodontic appliances, whether they use a key that uses a screw or a lever-like mechanism for activating the expansion of the acrylic halves. Some expansion screw devices may also have a directional arrow associated with them, to guide the patient when the need occurs to activate the expansion device, showing the direction for moving the lever or screw. As noted above, the expansion screw is centrally located and is partially embedded into each of the two acrylic halves, thereby keeping the bisected acrylic mold of the upper palate together in a singular functioning orthodontic appliance.

Method of Manufacture

The orthodontic appliance described above uses a set of two Hang Clasps, with one Hang Clasp on each side of the orthodontic appliance, as shown in FIGS. 1-5. A Hang Clasp may be manufactured using a heat treated stainless steel wire, cut to two essentially equal lengths, each length being approximately 3.5 inches long. The two lengths of wire are then spot welded together in place, nearer one end, about ¾ of the length from the end, at a set of angles between approximately 20° and 160° to between approximately 60° and 120°, typically about 45° and 135°, as per a patient's needs, to allow accurate placement of the wires for the solder joint. After a silver solder flux is placed on the weld/solder joint, a pin flame from a butane torch, or the like, is used to apply the solder. When applying the silver solder to the weld, one should be careful not to overheat the wire and to let solder flow and cool and then set, so as not to affect the strength of the wire. The four wires extending from the weld/solder joint are then bent at a rounded and non-sharp approximate right angle, so that the newly formed Hang Clasp, in its rough form, would fit over the desired molar of a patient. These four wire bends are the clasp wire bends.

A set of holes is then drilled into the model made of the patient's palate and teeth. Said model may be composed of a plaster, polymeric, rubber, or plastic material. Two holes are drilled on each side of the model in the upper primary second molar area where the wire ends of two of the four wire segments extending from the weld/solder joint will later be inserted on each side, said two wire ends being the mesial wire (86) and the distal wire (85).

A liquid separating medium, such as Liquid Foil Separator from Great Lakes Orthodontic Products, is then applied to the entire palate area of the upper model, to prevent acrylic from sticking to the upper model. A 3-prong pliers, or the like, is then used to bend and cut two adjacent wires on the Hang Clasps, hereinafter referred to as the mesial wire (86) and the distal wire (85) that are at an approximate angle of between approximately 120° and 160°, and cut to a length to be inserted into the model's two holes, referred to above, and made to fit between the two embrasures of the upper primary second molars.

The ends of the mesial wire (86) and the distal wire (85) are then ground and sharpened to points at the terminal ends of the wires, using a power green stone grinder or the like, to more easily fit these wires into the two embrasures of the upper primary second molars. The mesial wire point and the distal wire point allow the mesial wire (86) and the distal wire (85) to more easily fit into the embrasures of the tooth.

The two opposite wires on the Hang Clasp are the clasp anchors (83, 84) and each passes between the two embrasures of the tooth and are each bent behind the tooth with an anchor wire bend to where the end portions of the two clasp anchors are to be embedded in the acrylic. The end portion of each of the two clasp anchors are bent, using a 3-prong pliers, or the like, to form a plurality of crimps, or the like. These crimps further prevent the Hang Clasp from rotating or moving when in use, embedded in the acrylic portion of an orthodontic appliance.

When manufacturing the orthodontic appliance, sticky wax is then applied on all the wires intended to be in contact with the teeth and not intended to be embedded in the acrylic portion of the orthodontic appliance. Once the Hang Clasps and other elements of the orthodontic appliance have been embedded into the acrylic, prepared using a cold-cured or salt and pepper process, multiple times, where a special polymer powder is applied, followed by a special monomer fluid, which solidifies the acrylic, as desired. Instant hot water may then be applied to melt and thereby remove the sticky wax from the Hang Clasp, and the orthodontic appliance and the model. This step using sticky wax, in the manufacturing process, need not be done when solely manufacturing the Hang Clasp, or for the manufacture of the Hang Clasp for use in kits and the like, for later use in manufacturing an orthodontic appliance.

A method of manufacturing the Hang Clasp of the orthodontic appliance may be comprised essentially of the following steps:

a. measuring and cutting two wires, each approximately 3.5 inches long;

b. welding and then soldering said two wires together at an angle, about ¼ length from their ends, thereby forming a weld/solder joint;

c. gently bending the four wire segments extending from said weld/solder joint, to a rounded and non-sharp angle of approximately 90 degrees, thereby forming four clasp wire bends;

d. cutting two of said four wire segments that are adjacent to each other, thereby forming a mesial wire clasp and a distal wire clasp, with said mesial wire clasp and said distal wire clasp cut to a length to comfortably fit into the embrasures of a molar tooth, to clasp said tooth, when said Hang Clasp is fitted to the patient;

e. sharpening the end of the mesial wire to a mesial wire point and sharpening the end of the distal wire to a distal wire point;

f. cutting the two other adjacent wire segments of the four wire segments, thereby forming two anchor wires, to a length to properly anchor the Hang Clasp when embedded into an acrylic portion of an orthodontic appliance;

g. bending said two anchor wires near their ends, so that each of the anchor wires has a plurality of small crimps, or the like; and h. bending each of the two anchor wires, with an anchor wire bend, so that said anchor wires may be properly embedded into an acrylic portion of an orthodontic appliance.

Once a pair of Hang Clasps are manufactured, a set of holes are then drilled into the model made of the patient's upper palate and associated teeth. Said model may be composed of a plaster, polymeric, rubber, or plastic material. One hole is drilled in the middle of the palate area, to accommodate the expansion screw, and two additional holes are drilled on each side of the model in the upper primary second molar area where a Hang Clasp will be inserted on each side.

The symmetric midline of the upper model is then drawn, using a pencil or the like, to make sure that the expansion screw is inserted straight. A liquid separating medium, such as Liquid Foil Separator from Great Lakes Orthodontic Products, is then applied to the entire palate area of the upper model, to prevent acrylic from sticking to the upper model.

The advancer (14) its advancing wire (30) and advancing wire helices (32, 34) may also be made using 0.032 inch heat-treated stainless steel wire, or 0.036 TMA wire, that is bent to the shape as shown in FIGS. 1-4, using a 3-prong pliers or the like. The advancer (14) is periodically adjusted manually by an Orthodontist throughout the treatment of a patient, to properly advance the upper front teeth.

The advancing wire (30) has two advancing wire helices (32, 34) bent into it, using a 3-prong pliers or the like. The advancing wire helices (32, 34) decrease the force of the advancing wire (30) and increase the range of activity of the advancing wire (30) against the upper front teeth. The curve for the front teeth is first approximated by bending the wire about an appropriate curved surface that approximates the desired shape. The two ends of the advancer (14) that are to be embedded in the acrylic (16, 18) are the two advancing wire anchors (48, 50) and using a 3-prong pliers or the like, are bent with a plurality of crimps, or the like, so that the advancer (14) will not rotate or move when embedded in the acrylic 16, 18).

Sticky wax is then applied on all the wires intended to be in contact with the teeth and not intended to be embedded in the acrylic (16, 18) as indicated above in the disclosure relating to the manufacture of the Hang Clasp. The advancing wire helices (32, 34) are also covered with sticky wax so that the acrylic does not get into that portion of advancer (14).

Acrylic is then applied to the palatal region of the model, preferably using a so-called salt and pepper technique, a plurality of times. That is, each time, a special polymer powder is applied, followed by a special monomer fluid, which solidifies into acrylic.

The expansion screw is then set in place along the palatal midline. The acrylic is continued to be applied, preferably in excess of 10 millimeters, to make a ledge in the arch of the upper palate of the model, which allows the patient to use the orthodontic appliance when chewing and eating. There should be no acrylic on the areas where there is sticky wax. The acrylic is formed and molded to some extent using a spatula or the like. Excess monomer liquid is added to allow easier forming with the spatula. The model with the acrylic and embedded metal elements of the invention are then placed in a pressure pot so that it does not become porous and weakened. Instant hot water, or the like, is then applied to melt and thereby remove the sticky wax from the Orthodontic Appliance and the model.

The acrylic (16, 18) is then trimmed using a power grinder, or similar hand tool such as a power green stone grinder, starting with the mid-palate area where the expansion screw (20) is embedded in the acrylic (16, 18). The symmetric midline portion of the acrylic (16, 18) is then cut using a cutting tool, a drill or the like, so that the expansion screw (20) will function to expand the two acrylic halves (16, 18).

The acrylic is manually removed from the adjustment port (21) of the expansion screw (20) using a scalpel or a needle probe or the like, so that the expansion screw (20) may be adjusted as necessary. Some embodiments of the Orthodontic Appliance may indicate with an arrow or the like, the direction the expansion screw (20) is to be activated with a small key or lever. The Orthodontic Appliance is then polished and cleaned, and is ready to be more precisely adjusted and fit for use with the patient.

Kits for the Assembly of the Orthodontic Appliance

Kits for the manufacture and assembly of the orthodontic appliance may include the materials used in the method of manufacturing disclosed above, or may include some pre-assembled elements of the invention, or some partially assembled elements of the invention, or a combination thereof. Such pre-assembled elements may include a pre-assembled Hang Clasp, with its weld/solder joint, mesial wire, with or without the mesial wire point, distal wire, with or without the distal wire point, and two clasp anchors with crimps, or the like, and a pre-assembled advancer (14), with its advancing wire, two advancing wire helices, and two advancing wire anchors with crimps, or the like. A pre-prepared molar intrusion wire (26, 28) with its molar intrusion wire anchor, with crimps or helices, may also be included in such a kit.

These pre-assembled elements, along with pre-measured amounts of polymer and monomer for the acrylic formulation would make the use of the orthodontic appliance even easier to implement for Orthodontists. A kit may also include pre-measured amounts of the formulations and the tools to take a casting of the patient's upper teeth and palate. Present appliances require frequent adjustments and more visits to the orthodontic office, with their associated increased expense and inconvenience. The orthodontic appliance of this invention has a longer advancing wire, and an advancing wire helix, which mechanically reduces the force on the teeth and remains active longer, thereby requiring fewer orthodontic office visits.

The orthodontic appliance has one advancing wire (14) and its associated advancing wire helices (32, 34) to advance the front teeth with a very easy method of adjustment of the advancing wire (30). The advancer (14) is periodically adjusted manually by an Orthodontist throughout the treatment of a patient, to properly advance the upper front teeth.

The orthodontic appliance of this invention may be manufactured as disclosed above and variations may be made in the manufacture of the orthodontic appliance, such as in the gauge or type of wire used, to accommodate special patient needs or manufacturing efficiency. Some embodiments of the orthodontic appliance may exclude an element of the invention or a part thereof, or may include additional elements, or may include a minor variation of the elements disclosed herein. Such embodiments are intended to be covered by the present inventive concept and this patent.

The orthodontic appliances of this invention are useful and effective to accomplish craniofacial modification including correction of a maxillary deficiency or malocclusion, such as by expanding the maxillary arch and advancing the upper front teeth.

While only selected embodiments in accordance with the present invention are shown and described in this disclosure and its appended drawing figures, it is understood that the same is not limited thereto, but is susceptible to changes and modifications as known to one having ordinary skill in the art, and I therefore do not wish to be limited to the details shown and described herein, but instead to cover all such modifications, changes, eliminations, combinations and hybrids, as are encompassed by the scope of the appended claims, including, but not limited to kits, partial kits, or the like, for the manufacture of the orthodontic appliance, and further including pre-assembled or partially assembled kits for the manufacture of the orthodontic appliance.

Having thus described the invention, I claim:

1. An orthodontic appliance for expanding the maxillary arch and advancing the upper front teeth at the same time comprising:

a. a bisected acrylic upper palate mold, each hereinafter referred to as an acrylic half;

b. a centrally located expansion screw that is located between said two acrylic halves, and is partially embedded in each of the two acrylic halves;

c. an advancer located in a front region of said orthodontic appliance, said advancer consisting of a single wire, wound into three sections, an advancing wire section, in a half-oval shape adapted to press against the back of the upper front teeth, an advancing wire helix section, consisting of two helices, and a wire anchor section, consisting of two wire anchors, the two wire helices located between the rear of the advancing wire section and the front of the wire anchor section;

d. each of said two wire anchors partially embedded into a separate one of said acrylic halves;

e. two clasps, each of said clasps consisting of two substantially equal length wires soldered together at only one single point to form two substantially equal long ends and two substantially equal length short ends, the short ends bent into a shape adapted to create clasp anchors;

f. each of said clasp anchors being partially embedded into an acrylic half, with the two clasp anchors of each of said two clasps being partially embedded into a separate one of said two acrylic halves.

2. The orthodontic appliance of claim 1 further comprising two molar intrusion wires, each molar intrusion wire lies on the occlusal surface of a molar to the rear of a molar held by a clasp, each of the molar intrusion wires comprising a molar intrusion wire anchor located at one end of said molar intrusion wire, each said molar intrusion wire anchor being partially embedded into a separate one of the two acrylic halves.

3. The orthodontic appliance of claim 1, said wire anchors having a set of crimps located thereon.

4. The orthodontic appliance of claim 2, said molar intrusion wire anchors having a set of crimps located thereon.

5. An orthodontic appliance for expanding the maxillary arch and advancing the upper front teeth at the same time comprising a bisected acrylic mold of an upper palate, thereby comprising two acrylic halves with the following elements partially embedded therein:

a. a centrally located expansion screw partially embedded in each of said two acrylic halves;

b. a frontally located advancer partially embedded in each of the two acrylic halves;

c. two orthodontic molar clasps, each partially embedded in a separate acrylic half;

d. two molar intrusion wires, each partially embedded in a separate acrylic half, to the rear of each said orthodontic molar clasp;

e. said advancer consisting of a singlewire, first wound into a half-oval shape, then wound into two advancing wire helices, and then wound into two advancing wire anchors;

f. each of said orthodontic molar clasps consisting of two substantially equal length wires soldered together at a single point to form two substantially equal length long ends and two substantially equal length short ends, the short ends bent into a shape adapted to create a clasp around a molar and the two long ends adapted to create clasp anchors.

6. The orthodontic appliance of claim 1 or 5, in which the molar clasps are made of stainless steel wire.

* * * * *

UNITED STATES PATENT AND TRADEMARK OFFICE
CERTIFICATE OF CORRECTION

PATENT NO. : 9,011,145 B2
APPLICATION NO. : 12/731649
DATED : April 21, 2015
INVENTOR(S) : William M. Hang It is certified that error appears in the above-identified patent and that said Letters Patent is hereby corrected as shown below:

On the title page item (54) and in the specification col. 1, line 3,

-- Please delete the word "APPLICANCE" in the title and replace it with the word "APPLIANCE".
The correct title should read as follows:

"MAXILLARY EXPANSION AND ADVANCEMENT ORTHODONTIC APPLIANCE"

Signed and Sealed this
Sixth Day of October, 2015

Michelle K. Lee
*Director of the United States Patent and Trademark Office*